United States Patent [19]
Ni et al.

[11] Patent Number: 5,874,240
[45] Date of Patent: Feb. 23, 1999

[54] HUMAN 4-1BB RECEPTOR SPLICING VARIANT

[75] Inventors: Jian Ni, Rockville; Guo-Liang Yu, Darnestown; Reiner Gentz, Silver Spring; Patrick J. Dillon, Gaithersburg, all of Md.

[73] Assignee: Human Genome Sciences, Inc., Rockville, Md.

[21] Appl. No.: 816,605

[22] Filed: Mar. 13, 1997

Related U.S. Application Data

[60] Provisional application No. 60/013,474 Mar. 15, 1996.
[51] Int. Cl.$^6$ .......................... C12N 15/12; C12N 5/10; C07K 14/705
[52] U.S. Cl. ................. 435/69.1; 536/23.5; 536/23.1; 435/320.1; 435/325; 435/252.3; 435/254.11; 530/350; 530/395
[58] Field of Search .................. 536/23.5, 23.1; 530/350, 395; 435/69.1, 320.1, 325, 252.3, 254.11; 514/12, 2

[56] References Cited

U.S. PATENT DOCUMENTS 5,350,836  9/1994  Kopchick et al. ................ 530/399

FOREIGN PATENT DOCUMENTS

| 2108401 | 3/1995 | Canada . |
| 26290 | 11/1994 | WIPO . |
| 07984 | 3/1995 | WIPO . |
| 9733898 | 9/1997 | WIPO . |

OTHER PUBLICATIONS

Alderson et al., 1994, "Molecular and Biological Characterization of Human 4–1BB and its Ligand," *European Journal of Immunology* 24:2219–2227.

Goodwin et al., 1993, "Molecular Cloning of a Ligand for the Inducible T Cell Gene 4–1BB: A Member of an Emerging Family of Cytokines with Homology to Tumor Necrosis Factor," *European Journal of Immunology* 23:2631–2641.

Pollok et al., 1993, "Inducible T Cell Antigen 4–1BB," *Journal of Immunology* 150: 771–781.

Schwarz et al., 1993, "A Receptor Induced by Lymphocyte Activation (ILA): a New Member of the Human Nerve–Growth–Factor/Tumor–Necrosis–Factor Receptor Family," *Gene* 134:295–298.

Alderson et al., (Medline), US Natl. Lib. of Med., No. Q75424 (Nov. 24, 1994).

Kwon et al., (Medline), US Natl. Lib. of Med., No. R70977 (Mar. 23, 1995).

Alderson et al., (Medline), US Natl. Lib. of Med., No. Q07011, *Eur. J. Immunol.* 24:2219–2227(1994).

Schwarz et al., (Medline), US Natl. Lib. of Med., No. JT9752, *Gene* 134:295–298 (1993).

Zhou et al., *Immun. Ltrs.* 45:67–73 (1995).

*Primary Examiner*—Lorraine Spector
*Assistant Examiner*—Claire M. Kaufman
*Attorney, Agent, or Firm*—Kenley K. Hoover, Esq.

[57] ABSTRACT

The invention relates to h4-1BBSV receptor polypeptides, polynucleotides encoding the polypeptides, methods for producing the polypeptides, in particular by expressing the polynucleotides, and agonists and antagonists of the polypeptides. The invention further relates to methods for utilizing such polynucleotides, polypeptides, agonists and antagonists for applications, which relate, in part, to research, diagnostic and clinical arts.

37 Claims, 4 Drawing Sheets

```
                10                     30                     50
        GCACGAGGGAAAGTTCTCCGGCAGCCCTGAGATCTCAAGAGTGACATTTGTGAGACCAGC
                70                     90                     110
        TAATTTGATTAAAATTCTCTTGGAATCAGCTTTGCTAGTATCATACCTGTGCCAGATTTC
                130                    150                    170
        ATCATGGGAAACAGCTGTTACAACATAGTAGCCACTCTGTTGCTGGTCCTCAACTTTGAG
             M  G  N  S  C  Y  N  I  V  A  T  L  L  L  V  L  N  F  E
                190                    210                    230
        AGGACAAGATCATTGCAGGATCCTTGTAGTAACTGCCCAGCTGGTGTTTTCAGGACCAGG
         R  T  R  S  L  Q  D  P  C  S  N  C  P  A  G  V  F  R  T  R
                250                    270                    290
        AAGGAGTGTTCCTCCACCAGCAATGCAGAGTGTGACTGCACTCCAGGGTTTCACTGCCTG
         K  E  C  S  S  T  S  N  A  E  C  D  C  T  P  G  F  H  C  L
                310                    330                    350
        GGGGCAGGATGCAGCATGTGTGAACAGGATTGTAAACAAGGTCAAGAACTGACAAAAAAA
         G  A  G  C  S  M  C  E  Q  D  C  K  Q  G  Q  E  L  T  K  K
                370                    390                    410
        GGTTGTAAAGACTGTTGCTTTGGGACATTTAACGATCAGAAACGTGGCATCTGTCGACCC
         G  C  K  D  C  C  F  G  T  F  N  D  Q  K  R  G  I  C  R  P
                430                    450                    470
        TGGACAAACTGTTCTTTGGATGGAAAGTCTGTGCTTGTGAATGGGACGAAGGAGAGGGAC
         W  T  N  C  S  L  D  G  K  S  V  L  V  N  G  T  K  E  R  D
```

FIG.1A

```
                490                    510                     530
GTGGTCTGTGGACCATCTTCAGCCGACCTCTCTCCGGGAGCATCCTCTGTGACCCCGCCT
 V  V  C  G  P  S  S  A  D  L  S  P  G  A  S  S  V  T  P  P
                550                    570                     590
GCCCCTGCGAGAGAGCCAGGACACTCTCCGCAGATCATCTCCTTCTTTCTTGCGCTGACG
 A  P  A  R  E  P  G  H  S  P  Q  I  I  S  F  F  L  A  L  T
                                             _____
                610                    630                     650
TCGACTGCGTTGCTCTTCCTGCTGTTCTTCCTCACGCTCCGTTTCTCTGTTGTTAAACGG
 S  T  A  L  L  F  L  L  F  F  L  T  L  R  F  S  V  V  K  R
_____
                670                    690                     710
GGCAGAAAGAAACTCCTGTATATATTCAAACAACCATTTATGAGACCAGTACAAACTACT
 G  R  K  K  L  L  Y  I  F  K  Q  P  F  M  R  P  V  Q  T  T
                730                    750                     770
CAAGAGGAAGATGGCTGTAGCTGCCGATTTCCAGAAGAAGAAGAAGGAGGATGTGAACTG
 Q  E  E  D  G  C  S  C  R  F  P  E  E  E  E  G  G  C  E  L
                790                    810                     830
TGAAATGGAAGTCAATAGGGCTGTTGGGACTTTCTTGAAAAGAAGCAAGGAAATATGAGT
                850                    870                     890
CATCCGCTATCACAGCTTTCAAAAGCAAGAACAACATCCTACATTATACCCAGGATTCCC
                910                    930                     950
CCAACACACGTTCTTTTCTTAATGCCAATGAGTGGGCCTTTAAAAA
```

FIG.1B

```
  1 MGNSCYNIVATLLLVLNFERTRSLQDPCSNCPA.................  33
    |||||||||||||||||||||||||||||||||
  1 mgnscynivatlllvlnfertrslqdpcsncpagtfcdnnrnqicspcpp  50

34 ....................GVFRTRKECSSTSNAECDCTPGFHCLGAGCS  64
                        |||||||||||||||||||||||||||||||
 51 nsfssaggqrtcdicrqckgvfrtrkecsstsnaecdctpgfhclgagcs 100

65 MCEQDCKQGQELTKKGCKDCCFGTFNDQKRGICRPWTNCSLDGKSVLVNG 114
    |||||||||||||||||||||||||||||||||||||||||||||||||
101 mceqdckqgqeltkkgckdccfgtfndqkrgicrpwtncsldgksvlvng 150

115 TKERDVVCGPSSADLSPGASSVTPPAPAREPGHSPQIISFFLALTSTALL 164
    ||||||||||.|||||||||||||||||||||||||||||||||||||
151 tkerdvvcgpspadlspgassvtppaparepghspqiisfflaltstall 200

165 FLLFFLTLRFSVVKRGRKKLLYIFKQPFMRPVQTTQEEDGCSCRFPEEEE 214
    |||||||||||||||||||||||||||||||||||||||||||||||||
201 fllffltlrfsvvkrgrkkllyifkqpfmrpvqttqeedgcscrfpeeee 250

215 GGCEL 219
    |||||
251 ggcel 255
```

FIG.2

HUMAN 4-1BB RECEPTOR SPLICING VARIANT

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human 4-1BB receptor splicing variant, sometimes hereinafter referred to as "h4-1BBSV receptor".

This application claims benefit of 35 U.S.C. Section 120 based on copending U.S. provisional Application Serial No. 60/013474, filed Mar. 15, 1996.

BACKGROUND OF THE INVENTION

Many biological actions, for instance, response to certain stimuli and natural biological processes, are controlled by factors, such as cytokines. Many cytokines act through receptors by engaging the receptor and producing an intracellular response.

For example, tumor necrosis factor (TNF), both alpha and beta, are cytokines which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands there are included TNF-α, lymphotoxin-α (LT-α, also known as TNF-β, LT-β (found in complex heterotrimer LT-α2-β), FasL, CD40, CD27, CD30, 4-1BB, OX40 and nerve growth factor (NGF). The superfamily of TNF receptors includes the p55TNF receptor, p75TNF receptor, TNF receptor-related protein, FAS antigen or APL-1, CD40, CD27, CD30, 4-1BB, OX40, low affinity p75 and NGF-receptor (Meager, A., Biologicals, 22:291–295 (1994).

All members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (WatanabeFukunaga, R., et al., Nature, 356:314 (1992), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (Allen, R. C., et al., Science, 259:990 (1993). Targeted mutations of the low affinity nerve growth factor receptor cause a disorder characterized by faulty sensory innovation of peripheral structures (Lee, K. F., et al., Cell, 69:737 (1992).

TNF and LT-α are capable of binding to two TNF receptors (the 55- and 75-kd TNF receptors). A large number of biological effects elicited by TNF and LT-α, acting through their receptors, include hemorrhagic necrosis of transplanted tumors, cytotoxicity, a role in endotoxic shock, inflammation, immunoregulation, proliferation and antiviral responses, as well as protection against the deleterious effects of ionizing radiation. TNF and LT-α are involved in the pathogenesis of a wide range of diseases, including endotoxic shock, cerebral malaria, tumors, autoimmune disease, AIDS and graft-host rejection (Beutler, B. and Von Huffel, C., Science, 264:667, 668 (1994). Mutations in the p55 Receptor cause increased susceptibility to microbial infection.

4-1BB ligand, a member of the TNF family of ligands, is induced by T-cell activation. Signalling through a 4-1BB receptor enhances proliferative T-cell responses. Among known 4-1BB receptors is the inducible murine T-cell 4-1BB receptor which is a member of the TNF receptor family. It is expressed on activated T-cells as both a 30-kDa monomer and a 55-kDa homodimer (Pollok, K. E., et al., J. Immunol., 150:771 (1993). The 4-1BB receptor binds 4-1BB ligand with a high affinity, and has been identified and cloned (Goodwin, R. G., et al., Eur. J. Immunol., 23:2631 (1993). 4-1BB ligand was highly expressed on mature B and macrophage cell lines and anti-microactivated B-cells. Recently, the human homolog of the murine 4-1BB receptor and its ligand have been cloned (Schwarz, H. J., et al., Gene, 134:295 (1993). Data suggests a potential role for the interaction of 4-1BB receptor with its ligand in the process of T-cell activation.

A gene has also been recently identified which is induced by lymphocyte activation. The sequence of the full length 1.4 kb cDNA has been characterized as a new member of the nerve growth factor/tumor necrosis factor receptor family and is considered to be the human homolog of the murine T-cell-specific receptor 4-1BB. This receptor gene can be induced in lymphoid and differentiated non-lymphoid cell types. Expression of the protein encoded by this gene has been found on a subset of activated T or B lymphocytes. Activation-dependent expression of the protein is found not only in T lymphocytes, but also in B lymphocytes, monocytes and diverse non-lymphoid cell types (Schwarz, Blood, 85 (4):1043–1052 (1995).

The effects of TNF family ligands and TNF family receptors are varied and influence numerous functions, both normal and abnormal, in the biological processes of the mammalian system. There is a clear need, therefor, for identification and characterization of such receptors and ligands that influence biological activity, both normally and in disease states. In particular, there is a need to isolate and characterize additional NGF/TNF family receptors akin to 4-1BB which enhances proliferative T-cell responses and may be employed, therefore, for preventing, ameliorating or correcting dysfunctions or disease or augmenting positive natural actions of such receptors.

SUMMARY OF THE INVENTION

Toward these ends, and others, it is an object of the present invention to provide receptor polypeptides, inter alia, that have been identified as novel h4-1BBSV receptors by homology between the amino acid sequence set out in FIGS. 1A–B (SEQ ID NO:2) and known amino acid sequences of other proteins such as human the 4-1BB receptor protein which may have a different tissue distribution and a different specificity for 4-1BB ligand.

It is a further object of the invention, moreover, to provide polynucleotides that encode h4-1BBSV receptors, particularly polynucleotides that encode the polypeptide herein designated h4-1BBSV receptor.

In a particularly preferred embodiment of this aspect of the invention the polynucleotide comprises the region encoding h4-1BBSV receptor in the sequence set out in FIGS. 1A–B (SEQ ID NO:2).

In accordance with this aspect of the present invention there is provided an isolated nucleic acid molecule encoding a mature polypeptide expressed by the human cDNA contained in the deposited clone which is hereinafter described.

In accordance with this aspect of the invention there are provided isolated nucleic acid molecules encoding h4-1BBSV receptors, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of h4-1BBSV receptor.

In accordance with this aspect of the invention there are provided novel receptor polypeptides of human origin referred to herein as h4-1BBSV as well as biologically, diagnostically or therapeutically useful fragments, variants and derivatives thereof, variants and derivatives of the fragments, and analogs of the foregoing.

Among the particularly preferred embodiments of this aspect of the invention are variants of h4-1BBSV receptor encoded by naturally occurring alleles of the h4-1BBSV receptor gene.

It is another object of the invention to provide a process for producing the aforementioned polypeptides, polypeptide fragments, variants and derivatives, fragments of the variants and derivatives, and analogs of the foregoing. In a preferred embodiment of this aspect of the invention there are provided methods for producing the aforementioned h4-1BBSV receptor polypeptides comprising culturing host cells having expressibly incorporated therein an exogenously-derived h4-1BBSV-encoding polynucleotide under conditions for expression of h4-1BBSV receptor in the host and then recovering the expressed polypeptide.

In accordance with another object the invention there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing h4-1BBSV expression in cells by determining h4-1BBSV polypeptides or h4-1BBSV-encoding mRNA; assaying genetic variation and aberrations, such as defects, in h4-1BBSV genes; and administering a h4-1BBSV polypeptide or polynucleotide to an organism to augment h4-1BBSV function or remediate h4-1BBSV dysfunction.

In accordance with certain preferred embodiments of this and other aspects of the invention there are provided probes that hybridize to human h4-1BBSV sequences.

In certain additional preferred embodiments of this aspect of the invention there are provided antibodies against h4-1BBSV polypeptides. In certain particularly preferred embodiments in this regard, the antibodies are highly selective for h4-1BBSV.

In accordance with another aspect of the present invention, there are provided h4-1BBSV agonists. Among preferred agonists are molecules that bind to h4-1BBSV receptor molecules, and that elicit or augment h4-1BBSV receptor responses. Also among preferred agonists are molecules that interact with h4-1BBSV receptor polypeptides, or with other modulators of h4-1BBSV receptor activities, and thereby potentiate or augment an effect of h4-1BBSV receptor or more than one effect of h4-1BBSV receptor, for example, the agonists may be employed to treat and or prevent tumors, cytotoxicity, viral infection, deleterious effects of ionizing radiation, autoimmune disease, AIDS and graft-host rejection, to regulate immune responses, and cellular proliferation.

In accordance with yet another aspect of the present invention, there are provided h4-1BBSV antagonists. Among preferred antagonists are those which bind to h4-1BBSV receptor or binding molecules and do not elicit a h4-1BBSV receptor response or more than one h4-1BBSV receptor response. Also among preferred antagonists are soluble forms of the h4-1BBSV receptor which bind to or interact with ligands thereof so as to inhibit an effect of h4-1BBSV receptor or more than one effect of h4-1BBSV receptor or which prevent expression h4-1BBSV.

The antagonists may be used to inhibit the action of h4-1BBSV receptor polypeptides. They may be used, for instance, to treat and/or prevent endotoxic shock, inflammation, cerebral malaria, activation of the HIV virus, graft rejection, bone resorption and cachexia.

In a further aspect of the invention there are provided compositions comprising a h4-1BBSV receptor polynucleotide or a h4-1BBSV receptor polypeptide for administration to cells in vitro, to cells ex vivo and to cells in viva, or to a multicellular organism. In certain particularly preferred embodiments of this aspect of the invention, the compositions comprise a h4-1BBSV receptor polynucleotide for expression of a h4-1BBSV receptor polypeptide in a host organism for treatment of disease. Particularly preferred in this regard is expression in a human patient for treatment of a dysfunction associated with aberrant endogenous activity of h4-1BBSV receptor.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the nucleotide and deduced amino acid sequence of h4-1BBSV receptor.

FIG. 2 shows the regions of similarity between amino acid sequences of h4-1BBSV receptor (SEQ ID NO:2) and human 4-1BB receptor polypeptide as shown in Schwarz, H. J., et al., Gene, 134:295 (1993)(SEQ ID NO:9).

GLOSSARY

Figure 3:
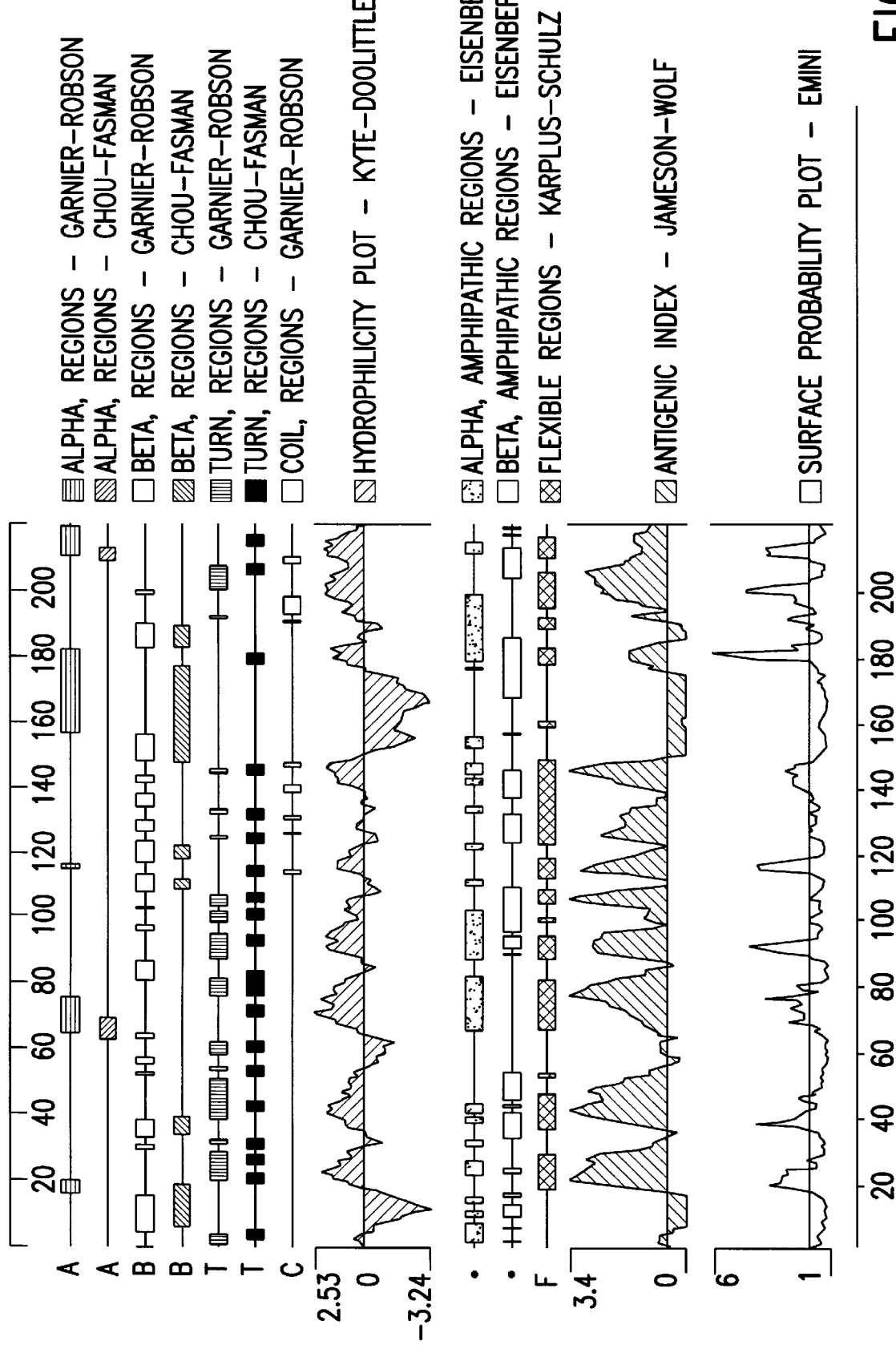
FIG. 3 shows structural and functional features of h4-1BBSV receptor deduced by the indicated techniques, as a function of amino acid sequence.

The following illustrative explanations are provided to facilitate understanding of certain terms used frequently herein, particularly in the examples. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 µg of plasmid or DNA fragment is digested with about 2 units of enzyme in about 20 µl of reaction buffer. For the purpose of isolating DNA fragments for plasmid construction, typically 5 to 50 µg of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

ISOLATED means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989) and Maniatis et al., pg. 146, as cited below.

OLIGONUCLEOTIDE(S) refers to relatively short polynucleotides. Often the term refers to single-stranded deoxyribonucleotide, but it can refer as well to single-or double-stranded ribonucleotide, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligase typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLASMIDS generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single-and double-stranded regions, single- and double-stranded RNA, and RNA that is mixture of single-and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Amng the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., Analysis for protein modifications and nonprotein cofactors, Meth. Enzymol. 182: 626–646 (1990) and Rattan et al., Protein Synthesis: Posttranslational Modifications and Aging, Ann. N.Y. Acad. Sci. 663: 48–62 (1992).

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

DESCRIPTION OF THE INVENTION

The present invention relates to novel h4-1BBSV receptor polypeptides and polynucleotides, among other things, as described in greater detail below. In particular, the invention relates to polypeptides and polynucleotides of a novel h4-1BBSV receptor, which is related by amino acid sequence homology to human h4-1BB receptor polypeptide (SEQ ID NO:9). The invention relates especially to h4-1BBSV receptor having the nucleotide and amino acid sequences set out in FIGS. 1A–B. (SEQ ID NO:1–2), and to the h4-1BBSV receptor nucleotide and amino acid sequences of the human cDNA in FIGS. 1A–B (SEQ ID NO:1) obtained by sequencing the cDNA of the deposited clone, hereinafter described. Hence, the sequence of the deposited clone is controlling as to any discrepancies between the two and any reference to the sequences of FIGS. 1A–B (SEQ ID NO:1) include reference to the sequence of the human cDNA of the deposited clone.

Polynucleotides

In accordance with one aspect of the present invention, there are provided isolated polynucleotides which encode the h4-1BBSV receptor polypeptide having the deduced amino acid sequence of FIGS. 1A–B (SEQ ID NO:2).

Using the information provided herein, such as the polynucleotide sequence set out in FIGS. 1A–B (SEQ ID NO:1), a polynucleotide of the present invention encoding h4-1BBSV receptor polypeptide may be obtained using standard cloning and screening procedures, such as those for cloning cDNAs using mRNA as starting material. Illustrative of the invention, the polynucleotide set out in FIGS. 1A–B (SEQ ID NO:1) was discovered in a cDNA library derived from cells of a human activated T-cell (12 hours)/ thiouridine labelled Eco.

h4-1BBSV receptor of the invention is structurally related to other proteins of the NGF Receptor family, as shown by the results of sequencing the human cDNA encoding h4-1BBSV receptor in the deposited clone, hereinafter described. The human cDNA sequence thus obtained is set out in FIGS. 1A–B (SEQ ID NO:1). It contains an open reading frame encoding a protein of about 219 amino acid residues with a deduced molecular weight of about 24.1 kDa. The initial 18 amino acids represent a putative leader sequence with the next 132 amino acids being a soluble extracellular domain and the next 27 amino acids being a transmembrane domain. The protein exhibits greatest degree of homology to human 4-1BB receptor protein among known proteins. The h4-1BBSV receptor of FIGS. 1A–B (SEQ ID NO:2) does not contain the second exon which encodes thirty-six amino acids, otherwise it is identical to the amino acid sequence of human 4-1BB receptor protein (SEQ ID NO:9).

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIGS. 1A–B (SEQ ID NO:1). It also may be a polynucleotide with a different sequence, which, as a result of the redundancy (degeneracy) of the genetic code, encodes the polypeptide of the DNA of FIGS. 1A–B (SEQ ID NO:2).

Polynucleotides of the present invention which encode the polypeptide of FIGS. 1A–B (SEQ ID NO:2) may include, but are not limited to the coding sequence for the mature polypeptide, by itself; the coding sequence for the mature polypeptide and additional coding sequences, such as those encoding a leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexahistidine peptide, such as the tag provided in a pQE vector (Qiagen, Inc.), among others, many of which are commercially available. As described in Gentz et al., Proc. Natl. Acad. Sci., USA 86: 821–824 (1989), for instance, hexa-histidine provides for convenient purification of the fusion protein. The HA tag corresponds to an epitope derived of influenza hemagglutinin protein, which has been described by Wilson et al., Cell 37: 767 (1984), for instance.

In accordance with the foregoing, the term "polynucleotide encoding a polypeptide" as used herein encompasses polynucleotides which include a sequence encoding a polypeptide of the present invention, particularly h4-1BBSV receptor having the amino acid sequence set out in FIGS. 1A–B (SEQ ID NO:2). The term encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptide having the deduced amino acid sequence of FIGS. 1A–B (SEQ ID NO:2). A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of h4-1BBSV receptor set out in FIGS. 1A–B (SEQ ID NO:2); variants, analogs derivatives and fragments thereof, and fragments of the variants, analogs and derivatives.

Further particularly preferred in this regard are polynucleotides encoding h4-1BBSV receptor variants, analogs, derivatives and fragments, and variants, analogs and derivatives of the fragments, which have the amino acid sequence of the h4-1BBSV receptor polypeptide of FIGS. 1A–B (SEQ ID NO:2) in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the h4-1BBSV receptor. Also especially preferred in this regard are conservative substitutions. Most highly preferred are polynucleotides encoding polypeptides having the amino acid sequence of FIGS. 1A–B (SEQ ID NO:2), without substitutions.

Further preferred embodiments of the invention are polynucleotides that are at least 70% identical to a polynucleotide encoding the h4-1BBSV receptor polypeptide having the amino acid sequence set out in FIGS. 1A–B (SEQ ID NO:2), and polynucleotides which are complementary to such polynucleotides. Alternatively, most highly preferred are polynucleotides that comprise a region that is at least 80% identical to a polynucleotide encoding the h4-1BBSV receptor polypeptide of the human cDNA of the deposited clone, hereinafter described, and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the mature polypeptide encoded by the human cDNA of FIGS. 1A–B (SEQ ID NO:1).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for cDNA and genomic DNA to isolate full-length cDNAs and genomic clones encoding h4-1BBSV receptor and to isolate cDNA and genomic clones of other genes that have a high sequence similarity to the h4-1BBSV receptor gene. Such probes generally will comprise at least 15 bases. Preferably, such probes will have at least 30 bases and may have at least 50 bases.

For example, the coding region of the h4-1BBSV receptor gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

In sum, a polynucleotide of the present invention may encode a mature protein, a mature protein plus a leader sequence (which may be referred to as a preprotein), a precursor of a mature protein having one or more prosequerces which are not the leader sequences of a preprotein, or a preproprotein, which is a precursor to a proprotein, having a leader sequence and one or more prosequences, which generally are removed during processing steps that produce active and mature forms of the polypeptide.

Deposited materials

A deposit containing a h4-1BBSV receptor cDNA has been deposited with the American Type Culture Collection, as noted above. The deposited clone was deposited with the American Type Culture Collection, 12301 Park Lawn Drive, Rockville, Md. 20852, USA, on Mar. 6, 1996 and assigned ATCC Deposit No. 97462.

The deposited clone is a pBluescript SK (–) plasmid (Stratagene, La Jolla, Calif.) that contains the full length h4-1BBSV receptor cDNA, referred to as "PF254" upon deposit.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a h4-1BBSV receptor polypeptide which has the deduced amino acid sequence of FIGS. 1A–B (SEQ ID NO:2).

The invention also relates to fragments, analogs and derivatives of these polypeptides. The terms "fragment," "derivative" and "analog" when referring to the polypeptide of FIGS. 1A–B (SEQ ID NO:2), means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

Among the particularly preferred embodiments of the invention in this regard are polypeptides having the amino acid sequence of h4-1BBSV receptor set out in FIGS. 1A–B (SEQ ID NO:2), variants, analogs, derivatives and fragments thereof, and variants, analogs and derivatives of the fragments. Alternatively, particularly preferred embodiments of the invention in this regard are polypeptides having the amino acid sequence of the h4-1BBSV receptor of the cDNA in the deposited clone, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the h4-1BBSV receptor polypeptide of FIGS. 1A–B (SEQ ID NO:2), in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the h4-1BBSV receptor. Also especially preferred in this regard are conservative substitutions. Most highly preferred are polypeptides having the amino acid sequence of FIGS. 1A–B (SEQ ID NO:2) without substitutions.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of h4-1BBSV receptor, most particularly fragments of the h4-1BBSV receptor having the amino acid set out in FIGS. 1A–B (SEQ ID NO:2), and fragments of variants and derivatives of the h4-1BBSV receptor of FIGS. 1A–B (SEQ ID NO:2).

In this regard a fragment is a polypeptide having an amino acid sequence that entirely is the same as part but not all of the amino acid sequence of the aforementioned h4-1BBSV receptor polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a h4-1BBSV receptor polypeptide of the present comprised within a precursor polypeptide designed for expression in a host and having heterologous pre and pro-polypeptide regions fused to the amino terminus of the h4-1BBSV receptor fragment and an additional region fused to the carboxyl terminus of the fragment. Therefore, fragments in one aspect of the meaning intended herein, refers to the portion or portions of a fusion polypeptide or fusion protein derived from h4-1BBSV receptor.

As representative examples of polypeptide fragments of the invention, there may be mentioned those which have from about 150 to about 219 amino acids.

In this context about includes the particularly recited range and ranges larger or smaller by several, a few, 5, 4, 3, 2 or 1 amino acid at either extreme or at both extremes. For instance, about 150 to about 219 amino acids in this context means a polypeptide fragment of 150 plus or minus several, a few, 5, 4, 3, 2 or 1 amino acids to 219 plus or minus several a few, 5, 4, 3, 2 or 1 amino acid residues, i.e., ranges as broad as 150 minus several amino acids to 219 plus several amino acids to as narrow as 150 plus several amino acids to 219 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 150 to about 219 amino acids.

Among especially preferred fragments of the invention are truncation mutants of h4-1BBSV receptor. Truncation mutants include h4-1BBSV receptor polypeptides having the amino acid sequence of FIGS. 1A–B (SEQ ID NO:2), or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are fragments characterized by structural or functional attributes of h4-1BBSV receptor. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of h4-1BBSV receptor.

Certain preferred regions in these regards are set out in FIG. 3, and include, but are not limited to, regions of the aforementioned types identified by analysis of the amino acid sequence set out in FIGS. 1A–B (SEQ ID NO:2). As set out in FIG. 3, such preferred regions include Garnier-Robson alpha-regions, beta-regions, turn-regions and coil-regions, Chou-Fasman alpha-regions, beta-regions and turn-regions, Kyte-Doolittle hydrophilic regions and hydrophilic regions, Eisenberg alpha and beta amphipathic regions, Karplus-Schulz flexible regions, Emini surface-forming regions and Jameson-Wolf high antigenic index regions.

Further preferred regions are those that mediate activities of h4-1BBSV receptor. Most highly preferred in this regard are fragments that have a chemical, biological or other activity of h4-1BBSV receptor, including those with a similar activity or an improved activity, or with a decreased undesirable activity. Highly preferred in this regard are fragments that contain regions that are homologs in sequence, or in position, or in both sequence and to active regions of related polypeptides, such as the related polypeptide set out in FIG. 2 (SEQ ID NO:9). Among particularly preferred fragments in these regards are truncation mutants, as discussed above.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Vectors, host cells, expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques. In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing E. coli and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are PWLNEO, pSV2CAT, pOG44, pXT1 and pSG available from Stratagene; and pSVK3, pBPV, PMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("cat") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the E. coli lacI and lacZ and promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of E. coli and the trpl gene of S. cerevisiae.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coli, Bacillus subtilis* and *Salmonella typhimurium.* Various species of Pseudomonas, Streptomyces, and Staphylococcus are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-7 lines of monkey kidney fibroblast, described in Gluzman et al., Cell 23: 175 (1981). Other cell lines capable of expressing a compatible vector include for example, the C127, 3T3, CHO, HeLa, human kidney 293 and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The h4-1BBSV receptor polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

h4-1BBSV receptor polynucleotides and polypeptides may be used in accordance with the present invention for a variety of applications, particularly those that make use of the chemical and biological properties h4-1BBSV receptor. Among these are applications in treatment of tumors, resistance to parasites, bacteria and viruses, to induce proliferation of endothelial cells and certain hematopoietic cells, to treat restenosis and to prevent certain autoimmune diseases after stimulation of an h4-1BBSV receptor by an agonist. Additional applications relate to diagnosis and to treatment of disorders of cells, tissues and organisms. These aspects of the invention are illustrated further by the following discussion.

Polynucleotide assays

This invention is also related to the use of the h4-1BBSV receptor polynucleotides to detect complementary polynucleotides such as, for example, as a diagnostic reagent. Detection of a mutated form of h4-1BBSV receptor associated with a dysfunction will provide a diagnostic tool that can add or define a diagnosis of a disease or susceptibility to a disease which results from under-expression over-expression or altered expression of h4-1BBSV receptor or a soluble form thereof, such as, for example, tumors, cytotoxicity, viral infection, autoimmune disease, AIDS and graft-host rejection.

Individuals carrying mutations in the h4-1BBSV receptor gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. (Saiki et al., Nature, 324: 163–166 (1986)). RNA or cDNA may also be used in the same ways. As an example, PCR primers complementary to the nucleic acid encoding h4-1BBSV receptor can be used to identify and analyze h4-1BBSV receptor expression and mutations. For example, deletions and insertions can be detected by a change in size of the amplified product in comparison to the normal genotype. Point mutations can be identified by hybridizing amplified DNA to radiolabeled h4-1BBSV receptor RNA or alternatively, radiolabeled h4-1BBSV receptor antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230: 1242 (1985)).

Sequence changes at specific locations also may be revealed by nuclease protection assays, such as RNase and S1 protection or the chemical cleavage method (e.g., Cotton et al., Proc. Natl. Acad. Sci., USA, 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Chromosome assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a h4-1BBSV receptor gene. This can be accomplished using a variety of well known techniques and libraries, which generally are available commercially. The genomic DNA the is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 50 or 60. For a review of this technique, see Verma et al., HUMAN CHROMOSOMES: A MANUAL OF BASIC TECHNIQUES, Pergamon Press, New York (1988).

Once a sequence has been mapped to a precise chromosomal location, the physical position of the sequence on the chromosome can be correlated with genetic map data. Such data are found, for example, in V. McKusick, MENDELIAN INHERITANCE IN MAN, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Polypeptide assays

The present invention also relates to diagnostic assays such as quantitative and diagnostic assays for detecting levels of h4-1BBSV receptor protein, or the soluble form thereof, in cells and tissues, including determination of normal and abnormal levels. Thus, for instance, a diagnostic assay in accordance with the invention for detecting overexpression of h4-1BBSV receptor, or soluble form thereof, compared to normal control tissue samples may be used to detect the presence of tumors, for example. Assay techniques that can be used to determine levels of a protein, such as an h4-1BBSV receptor protein of the present invention, or a soluble form thereof, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to h4-1BBSV receptor, or soluble form, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA assay, a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any h4-1BBSV receptor proteins attached to the polystyrene dish. Unbound monoclonal antibody is washed out with buffer. The reporter antibody linked to horseradish peroxidase is placed in the dish resulting in binding of the reporter antibody to any monoclonal antibody bound to h4-1BBSV receptor, or soluble receptor. Unattached reporter antibody is then washed out. Reagents. for peroxidase activity, including a calorimetric substrate are then added to the dish. Immobilized peroxidase, linked to h4-1BBSV receptor through the primary and secondary antibodies, produces a colored reaction product. The amount of color developed in a given time period indicates the amount of h4-1BBSV receptor protein, or soluble form, present in the sample. Quantitative results typically are obtained by reference to a standard curve.

A competition assay may be employed wherein antibodies specific to h4-1BBSV receptor, or soluble form, attached to a solid support and labeled h4-1BBSV receptor and a sample derived from the host are passed over the solid support and the amount of label detected attached to the solid support can be correlated to a quantity of h4-1BBSV receptor in the sample.

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., Nature 256: 495–497 (1975), the trioma technique, the human B-cell hybridoma technique (Kozbor et al., Immunology Today 4: 72 (1983) and the EBV-hybridoma technique to produce human monoclonal antibodies (Cole et al., pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or to purify the polypeptide of the present invention by attachment of the antibody to a solid support for isolation and/or purification by affinity chromatography.

h4-1BBSV receptor binding molecules and assays

The present invention provides a method for determining whether a ligand not known to be capable of binding to and h4-1BBSV receptor can bind to such receptor which comprises contacting a mammalian cell which expresses such a receptor with a ligand under conditions permitting binding of ligands to the receptor, detecting the presence of a ligand which binds to the receptor and thereby determining whether the ligand binds to the receptor. An example of such a method comprises contacting a mammalian cell comprising an isolated DNA molecule encoding the h4-1BBSV receptor with a plurality of candidate ligands, determining those ligands which bind to the receptor, and thereby identifying ligands which specifically interact with and bind to a receptor of the present invention.

Agonists and antagonists—assays and molecules

The invention also provides a method of screening compounds to identify those which enhance or block the action of h4-1BBSV receptor on cells. An agonist is a compound which increases the natural biological functions of h4-1BBSV receptor or which functions in a manner similar to h4-1BBSV while antagonists decrease or eliminate such functions.

In general, such screening procedures involve providing appropriate cells which express the receptor polypeptide of the present invention on the surface thereof. Such cells include cells from mammals, yeast, drosophila or *E. Coli*. In particular, a polynucleotide encoding the receptor of the present invention is employed to transfect cells to thereby express the receptor. The expressed receptor is then contacted with a test compound to observe binding, stimulation or inhibition of a functional response.

One such screening procedure involves the use of melanophores which are transfected to express the receptor of the present invention. Such a screening technique is described in PCT WO 92/01810 published Feb. 6, 1992.

Thus, for example, such assay may be employed for screening for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining a compound which activates the receptor by contacting such cells with compounds to be screened and determining whether such compound generates a signal, i.e., activates the receptor.

Other screening techniques include the use of cells which express the receptor (for example, transfected CHO cells) in a system which measures extracellular pH changes caused by receptor activation, for example, as described in Science, volume 246, pages 181–296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the receptor into *Xenopus oocytes* to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing the receptor in which the receptor is linked to a phospholipase C or D. As representative examples of such cells, there may be mentioned endothelial cells, smooth muscle cells, embryonic kidney cells, etc. The screening may be accomplished as hereinabove described by detecting activation of the receptor or inhibition of activation of the receptor from the phospholipase second signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing h4-1BBSV receptor-induced activities, thereby preventing the action of h4-1BBSV receptor by excluding h4-1BBSV receptor from binding. Examples of small molecules include but are not limited to small organic molecules, peptides or peptide-like molecules.

Other potential antagonists include antisense molecules. Antisense technology can be used to control gene expression through antisense DNA or RNA or through triple-helix formation. Antisense techniques are discussed, for example, in—Okano, J. Neurochem. 56: 560 (1991); OLIGODEOXY-NUCLEOTIDES AS ANTISENSE INHIBITORS OF GENE EXPRESSION, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of h4-1BBSV receptor. The antisense RNA oligonucleotide hybridizes to the mRNA in vivo and blocks translation of the mRNA molecule into h4-1BBSV receptor polypeptide. The oligonucleotides described above can also be delivered to cells such that the antisense RNA or DNA may be expressed in vivo to inhibit production of h4-1BBSV receptor.

A soluble form of the receptor, e.g. a fragment of the receptor, may be employed to inhibit activation of the receptor by binding to h4-1BBSV receptor ligand and preventing the ligand from interacting with membrane bound receptors.

The human 4-1BB receptor may also be employed as an antagonist. Antibodies specific to h4-1BBSV receptor polypeptide of the present invention are unique in that they may be used as both agonists and antagonists depending upon which portion, or epitope, of the receptor they are specific to as shown in published PCT Application WO 94/09137, which is hereby incorporated by reference. Fusing the soluble h4-1BBSV receptor to Fc or hinge regions of immunoglobulins will increase the half-life of h4-1BBSV in vivo and increase binding to ligand due to multimerization.

The antagonists may be employed in a composition with a pharmaceutically acceptable carrier, e.g., as hereinafter described.

The antagonists may be employed for instance to treat to prevent septic shock, inflammation, cerebral malaria, activation of the HIV virus, graft rejection, bone resorption and cachexia.

The agonists may be employed to treat and/or prevent tumors, restenosis, cytotoxicity, bacterial and viral infection, deleterious effects of ionizing radiation, autoimmune disease, AIDS and graft-host rejection, to regulate immune responses, wound healing and cellular proliferation.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 μg/kg body weight. In most cases they will be administered in an amount not in excess of about 8 mg/kg body weight per day. Preferably, in most cases, dose is from about 10 μg/kg to about 1 mg/kg body weight, daily. It will be appreciated that optimum dosage will be determined by standard methods for each treatment modality and indication, taking into account the indication, its severity, route of administration, complicating conditions and the like.

Gene therapy

The h4-1BBSV receptor polynucleotides, soluble form of the receptor polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller et al., Biotechniques 7: 980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin prompter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E-86, GP+envAm12, and DAN cell lines as described in Miller, A., Human Gene Therapy 1: 5–14 (1990). The vector may be transduced into the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989), herein referred to as "Sambrook."

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook and numerous other references such as, for instance, by Goeddel et al., Nucleic Acids Res. 8: 4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 μg of DNA.

Example 1

Expression and purification of human h4-1BBSV soluble extracellular domain using bacteria The DNA sequence encoding h4-1BBSV receptor in the deposited polynucleotide was amplified using PCR oligonucleotide primers specific to the amino acid carboxyl terminal sequence of the h4-1BBSV receptor protein and to vector sequences 3' to the gene. Additional nucleotides containing restriction sites to facilitate cloning were added to the 5' and 3' sequences respectively.

The 5' oligonucleotide primer had the sequence 5' CGC CCATGGGAGAGGACAAGATCA 3' (SEQ ID NO:3) containing the underlined NcoI restriction site, which encodes a start AUG, followed by 16 nucleotides of the h4-1BBSV receptor coding sequence set out in FIG. 1 (SEQ ID NO:1) after the signal peptide.

The 3' primer had the sequence 5' CGC GGTACCTCACTG CGGAGAGTG 3' (SEQ ID NO:4) containing the underlined Asp718 restriction site followed by 15 nucleotides complementary to the last 12 nucleotides of the h4-1BBSV receptor coding sequence for extracellular domain, including the stop codon.

The restrictions sites were convenient to restriction enzyme sites in the bacterial expression vectors pQE-70 which were used for bacterial expression in these examples. (Qiagen, Inc. 9259 Eton Avenue, Chatsworth, Calif., 91311). pQE-70 encodes ampicillin antibiotic resistance ("Ampr") and contains a bacterial origin of replication ("ori"), an IPTG inducible promoter, a ribosome binding site ("RBS"), a 6-His tag and restriction enzyme sites.

The amplified h4-1BBSV receptor DNA and the vector pQE-70 both were digested with NcoI and Asp718 and the digested DNAs then were ligated together. Insertion of the h4-1BBSV receptor DNA into the pQE-70 restricted vector placed the h4-1BBSV receptor coding region downstream of and operably linked to the vector's IPTG-inducible promoter and in-frame with an initiating AUG appropriately positioned for translation of h4-1BBSV receptor.

The ligation mixture was transformed into competent E. coli cells using standard procedures. Such procedures are described in Sambrook et al., MOLECULAR CLONING: A LABORATORY MANUAL, 2nd Ed.; Cold Spring Harbor Laboratory Press, Cold Spring Harbor, N.Y. (1989). E. coli strain M15/rep4, containing multiple copies of the plasmid pREP4, which expresses lac repressor and confers kanamycin resistance ("Kanr"), was used in carrying out the illustrative example described here. This strain, which is only one of many that are suitable for expressing h4-1BBSV receptor, is available commercially from Qiagen.

Transformants were identified by their ability to grow on LB plates in the presence of ampicillin. Plasmid DNA was isolated from resistant colonies and the identity of the cloned DNA was confirmed by restriction analysis.

Clones containing the desired constructs were grown overnight ("O/N") in liquid culture in LB media supplemented with both ampicillin (100 ug/ml) and kanamycin (25 ug/ml).

The O/N culture was used to inoculate a large culture, at a dilution of approximately 1:100 to 1:250. The cells were grown to an optical density at 600 nm ("OD600") of between 0.4 and 0.6. Isopropyl-B-D-thiogalactopyranoside ("IPTG") was then added to a final concentration of 1 mM to induce transcription from lac repressor sensitive promoters, by inactivating the laci repressor. Cells subsequently were incubated further for 3 to 4 hours. Cells then were harvested by centrifugation and disrupted, by standard methods. Inclusion bodies were purified from the disrupted cells using routine collection techniques, and protein was solubilized from the inclusion bodies into 8M urea. The 8M urea solution containing the solubilized protein was passed over a PD-10 column in 2X phosphate buffered saline ("PBS"), thereby removing the urea, exchanging the buffer and refolding the protein. The protein was purified by a further step of chromatography to remove endotoxin. Then, it was sterile filtered. The sterile filtered protein preparation was stored in 2X PBS at a concentration of 95 micrograms per mL.

Analysis of the preparation by standard methods of polyacrylamide gel electrophoresis revealed that the preparation contained about 90% monomer h4-1BBSV receptor having the expected molecular weight of, approximately, 14 kDa.

Example 2

Cloning and expression of the soluble extracellular domain h4-1BBSV receptor in a baculovirus expression system The cDNA sequence encoding the soluble extracellular domain of h4-1BBSV receptor protein in the deposited clone is amplified using PCR oligonucleotide primers corresponding to the 5' and 3' sequences of the gene:

The 5' primer has the sequence 5' CGC CCCGGGGCCATCATGGGA AACAGCTGT 3' (SEQ ID NO:5) containing the underlined Sma I restriction enzyme site followed by Kozak sequence and 15 bases of the sequence of h4-1BBSV receptor of FIG. 1 (SEQ ID NO:1). Inserted into an expression vector, as described below, the 5' end of the amplified fragment encoding h4-1BBSV receptor provides an efficient signal peptide. An efficient signal for initiation of translation in eukaryotic cells, as described by Kozak, M., J. Mol. Biol. 196: 947–950 (1987) is appropriately located in the primer portion of the construct. The 3' primer has the sequence 5' CGC GGTACCTCACTGCGGAGAGTG 3' (SEQ ID NO:6) containing the underlined Asp718 restriction followed by nucleotides complementary to bp 562 to 573 of the h4-1BBSV receptor coding sequence set out in FIGS. 1A–B (SEQ ID NO:1), including the stop codon.

The amplified fragment is isolated from a 1% agarose gel using a commercially available kit ("Geneclean," BIO 101 Inc., La Jolla, Calif.). The fragment then is digested with BamH1 and Asp718 and again is purified on a 1% agarose gel. This fragment is designated herein F2.

The vector pA2 is used to express the h4-1BBSV receptor protein in the baculovirus expression system, using standard methods, such as those described in Summers et al, A MANUAL OF METHODS FOR BACULOVIRUS VECTORS AND INSECT CELL CULTURE PROCEDURES, Texas Agricultural Experimental Station Bulletin No. 1555

(1987). This expression vector contains the strong polyhedrin promoter of the Autographa californica nuclear polyhedrosis virus (AcMNPV) followed by convenient restriction sites. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., Virology 170: 31–39, among others.

The plasmid is digested with the restriction enzymes Sma I and Asp718 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the human h4-1BBSV receptor gene by digesting DNA from individual colonies using Sma I and Asp718 and then analyzing the digestion product by gel electrophoresis. The sequence of the cloned fragment is confirmed by DNA sequencing. This plasmid is designated herein pBach4-1BBSV receptor.

5 $\mu$g of the plasmid pBach4-1BBSV receptor is co-transfected with 1.0 $\mu$g of a commercially available linearized baculovirus DNA ("BaculoGold™ baculovirus DNA", Pharmingen, San Diego, Calif.), using the lipofection method described by Felgner et al., Proc. Natl. Acad. Sci. USA 84: 7413–7417 (1987). 1 $\mu$g of BaculoGold™ virus DNA and 5 $\mu$g of the plasmid pBach4-1BBSV receptor are mixed in a sterile well of a microtiter plate containing 50 $\mu$l of serum free Grace's medium (Life Technologies Inc., Gaithersburg, Md.). Afterwards 10 $\mu$l Lipofectin plus 90 $\mu$l Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 $\mu$l of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted h4-1BBSV receptor is identified by DNA analysis including restriction mapping and sequencing. This is designated herein as V-h4-1BBSV receptor.

Sf9 cells are grown in Grace's medium supplemented with 10% heat-inactivated FBS. The cells are infected with the recombinant baculovirus V-h4-1BBSV receptor at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 $\mu$Ci of 35S-methionine and 5 $\mu$Ci 35S cysteine (available from Amersham) are added. The cells are further incubated for 16 hours and then they are harvested by centrifugation, lysed and the labeled proteins are visualized by SDS-PAGE and autoradiography.

Example 3

Expression of soluble extracellular domain h4-1BBSV receptor in COS cells

The expression plasmid, h4-1BBSV receptor HA, is made by cloning a cDNA encoding h4-1BBSV receptor into the expression vector pcDNAI/Amp (which can be obtained from Invitrogen, Inc.).

The expression vector pcDNAI/amp contains: (1) an *E. coli* origin of replication effective for propagation in *E. coli* and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire h4-1BBSV receptor precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., Cell 37: 767 (1984). The fusion of the HA tag to the target protein allows easy detection of the recombinant protein with an antibody that recognizes the HA epitope.

The plasmid construction strategy is as follows.

The h4-1BBSV receptor cDNA of the deposit clone is amplified using primers that contained convenient restriction sites, much as described above regarding the construction of expression vectors for expression of h4-1BBSV receptor in *E. coli* and *S. fugiperda*.

To facilitate detection, purification and characterization of the expressed h4-1BBSV receptor, one of the primers contains a hemagglutinin tag ("HA tag") as described above.

Suitable primers include that following, which are used in this example.

The 5' primer, 5' CGC GGATCCACCATGGGAAACAGCTGT 3' (SEQ ID NO:7)

contains the underlined Bam HI site, an ATG start codon and 12 codons thereafter.

The 3' primer, containing the underlined Xba I site and bp 562 to 573 of 3' coding sequence (at the 3' end) has the following sequence; 5' CGCTCTAGATCAAGCGTAGTC-TGGGACGTCGTATGGGTACTGCGGAGAGTG 3' (SEQ ID NO:8), the hemagglutinin tag is shown in bold.

The PCR amplified DNA fragment and the vector, pcDNAI/Amp, are digested with Bam HI and Xba I and then ligated. The ligation mixture is transformed into $E.$ $coli$ strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the h4-1BBSV receptor-encoding fragment.

For expression of recombinant h4-1BBSV receptor, COS cells are transfected with an expression vector, as described above, using DEAE-DEXTRAN, as described, for instance, in Sambrook et al., MOLECULAR CLONING: A LABORATORY MANUAL, Cold Spring Laboratory Press, Cold Spring Harbor, N.Y. (1989). Cells are incubated under conditions for expression of h4-1BBSV receptor by the vector.

Expression of the h4-1BBSV receptor HA fusion protein is detected by radiolabelling and immunoprecipitation, using methods described in, for example Harlow et al., ANTIBODIES: A LABORATORY MANUAL, 2nd Ed.; Cold Spring Harbor Laboratory Press, Cold Spring Harbor, N.Y. (1988). To this end, two days after transfection, the cells are labeled by incubation in media containing 35S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 4

Tissue distribution of h4-1BBSV receptor expression

Northern blot analysis is carried out to examine the levels of expression of h4-1BBSV receptor in human tissues, using methods described by, among others, Sambrook et al, cited above. Total cellular RNA samples are isolated with RNAzol™ B system (Biotecx Laboratories, Inc. 6023 South Loop East, Houston, Tex. 77033).

About 10 $\mu$g of Total RNA is isolated from tissue samples. The RNA is size resolved by electrophoresis through a 1% agarose gel under strongly denaturing conditions. RNA is blotted from the gel onto a nylon filter, and the filter then is prepared for hybridization to a detectably labeled polynucleotide probe.

As a probe to detect mRNA that encodes h4-1BBSV receptor, the antisense strand of the coding region of the cDNA insert in the deposited clone is labeled to a high specific activity. The cDNA is labeled by primer extension, using the Prime-It kit, available from Stratagene. The reaction is carried out using 50 ng of the cDNA, following the standard reaction protocol as recommended by the supplier. The labeled polynucleotide is purified away from other labeled reaction components by column chromatography using a Select-G-50 column, obtained from 5-Prime–3-Prime, Inc. of 5603 Arapahoe Road, Boulder, Colo. 80303.

The labeled probe is hybridized to the filter, at a concentration of 1,000,000 cpm/ml, in a small volume of 7% SDS, 0.5M NaPO4, pH 7.4 at 65° C., overnight.

Thereafter the probe solution is drained and the filter is washed twice at room temperature and twice at 60° C. with 0.5×SSC, 0.1% SDS. The filter then is dried and exposed to film at −70° C. overnight with an intensifying screen.

Example 5

Gene therapeutic expression of human h4-1BBSV receptor

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

h4-1BBSV cDNA capable of expressing active h4-1BBSV receptor, is isolated. The ends of the fragment are modified, if necessary, for cloning into the vector. For instance, 5" overhanging may be treated with DNA polymerase to create blunt ends. 3' overhanging ends may be removed using S1 nuclease. Linkers may be ligated to blunt ends with T4 DNA ligase.

Equal quantities of the Moloney murine leukemia virus linear backbone and the h4-1BBSV receptor fragment are mixed together and joined using T4 DNA ligase. The ligation mixture is used to transform *E. Coli* and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the h4-1BBSV receptor gene is introduced into the packaging cells by standard techniques. Infectious viral particles containing the h4-1BBSV receptor gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce h4-1BBSV receptor product, and the biological actions of the protein are conveyed to the host.

It will be clear that the invention may be practiced otherwise than as particularly described in the foregoing description and examples.

Numerous modifications and variations of the present invention are possible in light of the above teachings and, therefore, are within the scope of the appended claims.

What is claimed is:

1. An isolated nucleic acid comprising a member selected from the group consisting of:
   (a) a polynucleotide encoding amino acids −18 to 201 of SEQ ID NO:2;
   (b) a polynucleotide encoding amino acids −17 to 201 of SEQ ID NO:2;
   (c) a polynucleotide encoding amino acids 1 to 201 of SEQ ID NO:2;
   (d) a polynucleotide encoding amino acids 1 to 132 of SEQ ID NO:2; and
   (e) a polynucleotide complementary to the polynucleotide of (a), (b), (c), or (d).

2. The isolated polynucleotide of claim 1 wherein said member is (a).

3. The isolated polynucleotide of claim 1 wherein said member is (b).

4. The isolated polynucleotide of claim 1 wherein said member is (c).

5. The isolated polynucleotide of claim 1 wherein said member is (d).

6. The isolated polynucleotide of claim 1 wherein the isolated polynucleotide is RNA.

7. A method of making a recombinant vector comprising inserting the isolated polynucleotide of claim 1 into a vector, wherein said polynucleotide is DNA.

8. A recombinant vector comprising the isolated polynucleotide of claim 1, wherein said polynucleotide is DNA.

9. A recombinant host cell comprising the vector of claim 8 comprising said isolated polynucleotide.

10. The isolated polynucleotide of claim 5 comprising the nucleotides 178 to 573 of SEQ ID NO:1.

11. The isolated polynucleotide of claim 5 comprising the nucleotides 1 to 946 of SEQ ID NO:1.

12. The isolated polynucleotide of claim 2 comprising the nucleotides 124 to 780 of SEQ ID NO:1.

13. An expression vector comprising the nucleic acid of claim 1 in operative association with a nucleotide regulatory sequence that controls the expression of the nucleotide sequence in a host.

14. An isolated nucleic acid comprising a polynucleotide selected from the group consisting of:
   (a) a polynucleotide encoding the full-length polypeptide encoded by the human cDNA contained in ATCC Deposit No. 97462;
   (b) a polynucleotide encoding the full-length polypeptide encoded by the human cDNA contained in ATCC Deposit No. 97462, excepting the N-terminal methionine;
   (c) a polynucleotide encoding a mature polypeptide encoded by the human cDNA contained in ATCC Deposit No. 97462; and
   (d) a polynucleotide complementary to the polynucleotide of (a), (b) or (c).

15. The isolated polynucleotide of claim 14 wherein said member is (b).

16. The isolated polynucleotide of claim 14 wherein said member is (c).

17. The isolated polynucleotide of claim 14 wherein said member is DNA.

18. A method of making a recombinant vector comprising inserting the isolated polynucleotide of claim 14 into a vector, wherein said polynucleotide is DNA.

19. A recombinant vector comprising the isolated polynucleotide of claim 14 wherein said polynucleotide is DNA.

20. A recombinant host cell comprising the vector of claim 19 comprising said isolated polynucleotide.

21. An isolated polypeptide comprising a polypeptide member selected from the group consisting of:
   (a) amino acids −18 to 201 in SEQ ID NO:2;
   (b) amino acids −17 to 201 in SEQ ID NO:2;
   (c) amino acids 1 to 201 in SEQ ID NO:2; and
   (d) amino acids 1 to 132 in SEQ ID NO:2.

22. The isolated polypeptide of claim 21 wherein said member is (c).

23. The isolated polypeptide of claim 21 wherein said member is (d).

24. A composition comprising a polypeptide of claim 21 and a pharmaceutically acceptable carrier.

25. An isolated polypeptide comprising a polypeptide member selected from the group consisting of:
   (a) the full-length polypeptide encoded by the human cDNA clone contained in ATCC Deposit No. 97462;
   (b) the full-length polypeptide encoded by the human cDNA clone contained in ATCC Deposit No. 97462 excepting the N-terminal methionine; and
   (c) the mature polypeptide encoded by the human cDNA clone contained in ATCC Deposit No. 97462.

26. The isolated polypeptide of claim 25 wherein said member is (b).

27. The isolated polypeptide of claim 25 wherein said member is (c).

28. A composition comprising a polypeptide of claim 25 and a pharmaceutically acceptable carrier.

29. An isolated deletion variant of human 4-1BB receptor having the sequence of SEQ ID NO:9 from which amino acid residues 34–69 have been deleted, and optionally comprising an alteration selected from the group consisting of:
   a) substitution or deletion of an additional 1–10 amino acid residues of SEQ ID NO:9, and
   b) insertion of 1–10 amino acid residues in a region other than the region consisting of amino acid residues 34–69 of SEQ ID NO:9.

30. An isolated extracellular domain of a deletion variant of human 4-1BB receptor having the sequence of SEQ ID NO:9 from of amino acids 19–205 from which amino acid residues 34–69 have been deleted, and optionally comprising an alteration selected from the group consisting of:
   a) substitution or deletion of an additional 1–10 amino acid residues of SEQ ID NO:9, and
   b) insertion of 1–10 amino acid residues in a region other than the region consisting of amino acid residues 34–69 of SEQ ID NO:9.

31. A composition comprising a deletion variant of claim 29 or an extracellular domain of claim 30 and a pharmaceutically acceptable carrier.

32. An isolated nucleic acid comprising a polynucleotide which encodes a deletion variant of human 4-1BB receptor having the sequence of SEQ ID NO:9 from which amino acid residues 34–69 have been deleted, and optionally comprising an alteration selected from the group consisting of:
   a) substitution or deletion of an additional 1–10 amino acid residues of SEQ ID NO:9, and
   b) insertion of 1–10 amino acid residues in a region other than the region consisting of amino acid residues 34–69 of SEQ ID NO:9.

33. An isolated nucleic acid comprising a polynucleotide which encodes the extracellular domain of a deletion variant of human 4-1BB receptor having the sequence of SEQ ID NO:9 from of amino acids 19–205 from which amino acid residues 34–69 have been deleted, and optionally comprising an alteration selected from the group consisting of:
   a) substitution or deletion of an additional 1–10 amino acid residues of SEQ ID NO:9, and
   b) insertion of 1–10 amino acid residues in a region other than the region consisting of amino acid residues 34–69 of SEQ ID NO:9.

34. A method of making a recombinant vector comprising inserting the isolated nucleic acid of claim 32 or 33 into a vector, wherein said nucleic acid is DNA.

35. A recombinant vector comprising the isolated nucleic acid of claim 32 or 33, wherein said nucleic acid is DNA.

36. A recombinant host cell comprising the vector of claim 35 comprising said isolated nucleic acid.

37. An expression vector comprising the nucleic acid of claim 32 or 33 in operative association with a nucleotide regulatory sequence that controls the expression of the nucleotide sequence in a host.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 946 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 124..780

( i x ) FEATURE:
        ( A ) NAME/KEY: sig_peptide
        ( B ) LOCATION: 124..177

( i x ) FEATURE:
        ( A ) NAME/KEY: mat_peptide
        ( B ) LOCATION: 178..780

( x i ) SEQUENCE DESCRIPTION: SEQ ID NO:1:

```
GCACGAGGGA  AAGTTCTCCG  GCAGCCCTGA  GATCTCAAGA  GTGACATTTG  TGAGACCAGC      60

TAATTTGATT  AAAATTCTCT  TGGAATCAGC  TTTGCTAGTA  TCATACCTGT  GCCAGATTTC     120

ATC  ATG  GGA  AAC  AGC  TGT  TAC  AAC  ATA  GTA  GCC  ACT  CTG  TTG  CTG  GTC     168
     Met  Gly  Asn  Ser  Cys  Tyr  Asn  Ile  Val  Ala  Thr  Leu  Leu  Leu  Val
     -18            -15                      -10                        -5

CTC  AAC  TTT  GAG  AGG  ACA  AGA  TCA  TTG  CAG  GAT  CCT  TGT  AGT  AAC  TGC     216
Leu  Asn  Phe  Glu  Arg  Thr  Arg  Ser  Leu  Gln  Asp  Pro  Cys  Ser  Asn  Cys
                    1              5                        10

CCA  GCT  GGT  GTT  TTC  AGG  ACC  AGG  AAG  GAG  TGT  TCC  TCC  ACC  AGC  AAT     264
Pro  Ala  Gly  Val  Phe  Arg  Thr  Arg  Lys  Glu  Cys  Ser  Ser  Thr  Ser  Asn
        15                        20                       25

GCA  GAG  TGT  GAC  TGC  ACT  CCA  GGG  TTT  CAC  TGC  CTG  GGG  GCA  GGA  TGC     312
Ala  Glu  Cys  Asp  Cys  Thr  Pro  Gly  Phe  His  Cys  Leu  Gly  Ala  Gly  Cys
 30                      35                       40                       45

AGC  ATG  TGT  GAA  CAG  GAT  TGT  AAA  CAA  GGT  CAA  GAA  CTG  ACA  AAA  AAA     360
Ser  Met  Cys  Glu  Gln  Asp  Cys  Lys  Gln  Gly  Gln  Glu  Leu  Thr  Lys  Lys
                         50                        55                       60

GGT  TGT  AAA  GAC  TGT  TGC  TTT  GGG  ACA  TTT  AAC  GAT  CAG  AAA  CGT  GGC     408
Gly  Cys  Lys  Asp  Cys  Cys  Phe  Gly  Thr  Phe  Asn  Asp  Gln  Lys  Arg  Gly
                65                        70                       75

ATC  TGT  CGA  CCC  TGG  ACA  AAC  TGT  TCT  TTG  GAT  GGA  AAG  TCT  GTG  CTT     456
Ile  Cys  Arg  Pro  Trp  Thr  Asn  Cys  Ser  Leu  Asp  Gly  Lys  Ser  Val  Leu
          80                        85                       90

GTG  AAT  GGG  ACG  AAG  GAG  AGG  GAC  GTG  GTC  TGT  GGA  CCA  TCT  TCA  GCC     504
Val  Asn  Gly  Thr  Lys  Glu  Arg  Asp  Val  Val  Cys  Gly  Pro  Ser  Ser  Ala
```

|      |      |      |      |      |      |      |      |      |      |      |      |      |      |      |      |     |
|------|------|------|------|------|------|------|------|------|------|------|------|------|------|------|------|-----|
|      |      | 95   |      |      |      | 100  |      |      |      |      | 105  |      |      |      |      |     |
| GAC  | CTC  | TCT  | CCG  | GGA  | GCA  | TCC  | TCT  | GTG  | ACC  | CCG  | CCT  | GCC  | CCT  | GCG  | AGA  | 552 |
| Asp  | Leu  | Ser  | Pro  | Gly  | Ala  | Ser  | Ser  | Val  | Thr  | Pro  | Pro  | Ala  | Pro  | Ala  | Arg  |     |
| 110  |      |      |      |      | 115  |      |      |      |      | 120  |      |      |      |      | 125  |     |
| GAG  | CCA  | GGA  | CAC  | TCT  | CCG  | CAG  | ATC  | ATC  | TCC  | TTC  | TTT  | CTT  | GCG  | CTG  | ACG  | 600 |
| Glu  | Pro  | Gly  | His  | Ser  | Pro  | Gln  | Ile  | Ile  | Ser  | Phe  | Phe  | Leu  | Ala  | Leu  | Thr  |     |
|      |      |      |      | 130  |      |      |      |      | 135  |      |      |      |      | 140  |      |     |
| TCG  | ACT  | GCG  | TTG  | CTC  | TTC  | CTG  | CTG  | TTC  | TTC  | CTC  | ACG  | CTC  | CGT  | TTC  | TCT  | 648 |
| Ser  | Thr  | Ala  | Leu  | Leu  | Phe  | Leu  | Leu  | Phe  | Phe  | Leu  | Thr  | Leu  | Arg  | Phe  | Ser  |     |
|      |      |      |      | 145  |      |      |      |      | 150  |      |      |      |      | 155  |      |     |
| GTT  | GTT  | AAA  | CGG  | GGC  | AGA  | AAG  | AAA  | CTC  | CTG  | TAT  | ATA  | TTC  | AAA  | CAA  | CCA  | 696 |
| Val  | Val  | Lys  | Arg  | Gly  | Arg  | Lys  | Lys  | Leu  | Leu  | Tyr  | Ile  | Phe  | Lys  | Gln  | Pro  |     |
|      |      | 160  |      |      |      | 165  |      |      |      |      | 170  |      |      |      |      |     |
| TTT  | ATG  | AGA  | CCA  | GTA  | CAA  | ACT  | ACT  | CAA  | GAG  | GAA  | GAT  | GGC  | TGT  | AGC  | TGC  | 744 |
| Phe  | Met  | Arg  | Pro  | Val  | Gln  | Thr  | Thr  | Gln  | Glu  | Glu  | Asp  | Gly  | Cys  | Ser  | Cys  |     |
|      |      | 175  |      |      |      | 180  |      |      |      |      | 185  |      |      |      |      |     |
| CGA  | TTT  | CCA  | GAA  | GAA  | GAA  | GAA  | GGA  | GGA  | TGT  | GAA  | CTG  | TGAAATGGAA |  |  |  | 790 |
| Arg  | Phe  | Pro  | Glu  | Glu  | Glu  | Glu  | Gly  | Gly  | Cys  | Glu  | Leu  |      |      |      |      |     |
| 190  |      |      |      |      | 195  |      |      |      |      | 200  |      |      |      |      |      |     |

| | | | |
|---|---|---|---|
| GTCAATAGGG | CTGTTGGGAC | TTTCTTGAAA | AGAAGCAAGG  AAATATGAGT  CATCCGCTAT | 850 |
| CACAGCTTTC | AAAAGCAAGA | ACAACATCCT | ACATTATACC  CAGGATTCCC  CCAACACACG | 910 |
| TTCTTTTCTT | AATGCCAATG | AGTGGGCCTT | TAAAAA | 946 |

( 2 ) INFORMATION FOR SEQ ID NO:2:

( i ) SEQUENCE CHARACTERISTICS:
        ( A ) LENGTH: 219 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Gly | Asn | Ser | Cys | Tyr | Asn | Ile | Val | Ala | Thr | Leu | Leu | Leu | Val | Leu |
| -18 |     | -15 |     |     |     |     | -10 |     |     |     |     | -5  |     |     |     |
| Asn | Phe | Glu | Arg | Thr | Arg | Ser | Leu | Gln | Asp | Pro | Cys | Ser | Asn | Cys | Pro |
|     |     | 1   |     |     |     | 5   |     |     |     |     | 10  |     |     |     |     |
| Ala | Gly | Val | Phe | Arg | Thr | Arg | Lys | Glu | Cys | Ser | Ser | Thr | Ser | Asn | Ala |
| 15  |     |     |     |     | 20  |     |     |     |     | 25  |     |     |     |     | 30  |
| Glu | Cys | Asp | Cys | Thr | Pro | Gly | Phe | His | Cys | Leu | Gly | Ala | Gly | Cys | Ser |
|     |     |     |     | 35  |     |     |     |     | 40  |     |     |     |     | 45  |     |
| Met | Cys | Glu | Gln | Asp | Cys | Lys | Gln | Gly | Gln | Glu | Leu | Thr | Lys | Lys | Gly |
|     |     |     |     | 50  |     |     |     |     | 55  |     |     |     |     | 60  |     |
| Cys | Lys | Asp | Cys | Cys | Phe | Gly | Thr | Phe | Asn | Asp | Gln | Lys | Arg | Gly | Ile |
|     |     |     |     | 65  |     |     |     |     | 70  |     |     |     |     | 75  |     |
| Cys | Arg | Pro | Trp | Thr | Asn | Cys | Ser | Leu | Asp | Gly | Lys | Ser | Val | Leu | Val |
|     |     | 80  |     |     |     | 85  |     |     |     |     | 90  |     |     |     |     |
| Asn | Gly | Thr | Lys | Glu | Arg | Asp | Val | Val | Cys | Gly | Pro | Ser | Ser | Ala | Asp |
| 95  |     |     |     |     | 100 |     |     |     |     | 105 |     |     |     |     | 110 |
| Leu | Ser | Pro | Gly | Ala | Ser | Ser | Val | Thr | Pro | Pro | Ala | Pro | Ala | Arg | Glu |
|     |     |     |     | 115 |     |     |     |     | 120 |     |     |     |     | 125 |     |
| Pro | Gly | His | Ser | Pro | Gln | Ile | Ile | Ser | Phe | Phe | Leu | Ala | Leu | Thr | Ser |
|     |     |     |     | 130 |     |     |     |     | 135 |     |     |     |     | 140 |     |
| Thr | Ala | Leu | Leu | Phe | Leu | Leu | Phe | Phe | Leu | Thr | Leu | Arg | Phe | Ser | Val |
|     |     |     |     | 145 |     |     |     |     | 150 |     |     |     |     | 155 |     |
| Val | Lys | Arg | Gly | Arg | Lys | Lys | Leu | Leu | Tyr | Ile | Phe | Lys | Gln | Pro | Phe |
|     |     | 160 |     |     |     | 165 |     |     |     |     | 170 |     |     |     |     |

| Met | Arg | Pro | Val | Gln | Thr | Thr | Gln | Glu | Glu | Asp | Gly | Cys | Ser | Cys | Arg |
| 175 | | | | | 180 | | | | | 185 | | | | | 190 |

| Phe | Pro | Glu | Glu | Glu | Glu | Gly | Gly | Cys | Glu | Leu |
| | | | | 195 | | | | 200 | | |

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CGCCCATGGG AGAGGACAAG ATCA        24

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CGCGGTACCT CACTGCGGAG AGTG        24

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGCCCCGGGG CCATCATGGG AAACAGCTGT        30

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CGCGGTACCT CACTGCGGAG AGTG        24

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CGCGGATCCA CCATGGGAAA CAGCTGT        27

( 2 ) INFORMATION FOR SEQ ID NO:8:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CGCTCTAGAT CAAGCGTAGT CTGGGACGTC GTATGGGTAC TGCGGAGAGT G    51

( 2 ) INFORMATION FOR SEQ ID NO:9:

( i ) SEQUENCE CHARACTERISTICS:
        ( A ) LENGTH: 255 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Met Gly Asn Ser Cys Tyr Asn Ile Val Ala Thr Leu Leu Leu Val Leu
 1               5                  10                  15
Asn Phe Glu Arg Thr Arg Ser Leu Gln Asp Pro Cys Ser Asn Cys Pro
                20                  25                  30
Ala Gly Thr Phe Cys Asp Asn Asn Arg Asn Gln Ile Cys Ser Pro Cys
            35                  40                  45
Pro Pro Asn Ser Phe Ser Ser Ala Gly Gly Gln Arg Thr Cys Asp Ile
50                  55                  60
Cys Arg Gln Cys Lys Gly Val Phe Arg Thr Arg Lys Glu Cys Ser Ser
65                  70                  75                  80
Thr Ser Asn Ala Glu Cys Asp Cys Thr Pro Gly Phe His Cys Leu Gly
                85                  90                  95
Ala Gly Cys Ser Met Cys Glu Gln Asp Cys Lys Gln Gly Gln Glu Leu
            100                 105                 110
Thr Lys Lys Gly Cys Lys Asp Cys Cys Phe Gly Thr Phe Asn Asp Gln
            115                 120                 125
Lys Arg Gly Ile Cys Arg Pro Trp Thr Asn Cys Ser Leu Asp Gly Lys
    130                 135                 140
Ser Val Leu Val Asn Gly Thr Lys Glu Arg Asp Val Val Cys Gly Pro
145                 150                 155                 160
Ser Pro Ala Asp Leu Ser Pro Gly Ala Ser Ser Val Thr Pro Pro Ala
                165                 170                 175
Pro Ala Arg Glu Pro Gly His Ser Pro Gln Ile Ile Ser Phe Phe Leu
            180                 185                 190
Ala Leu Thr Ser Thr Ala Leu Leu Phe Leu Leu Phe Phe Leu Thr Leu
            195                 200                 205
Arg Phe Ser Val Val Lys Arg Gly Arg Lys Lys Leu Leu Tyr Ile Phe
    210                 215                 220
Lys Gln Pro Phe Met Arg Pro Val Gln Thr Thr Gln Glu Glu Asp Gly
225                 230                 235                 240
Cys Ser Cys Arg Phe Pro Glu Glu Glu Glu Gly Gly Cys Glu Leu
                245                 250                 255
```